United States Patent
Cameron et al.

(10) Patent No.: US 6,888,303 B2
(45) Date of Patent: May 3, 2005

(54) ULTRAVIOLET TANNING SYSTEMS

(75) Inventors: Mickey G. Cameron, Greenwood, IN (US); Roy L. Griffith, Indianapolis, IN (US); Chris P. Baird, Indianapolis, IN (US)

(73) Assignee: ETS, Inc., Indianapolis, IN (US)

( * ) Notice: Subject to any disclaimer, the term of this patent is extended or adjusted under 35 U.S.C. 154(b) by 175 days.

(21) Appl. No.: 10/287,415

(22) Filed: Nov. 4, 2002

(65) Prior Publication Data

US 2004/0088028 A1 May 6, 2004

(51) Int. Cl.$^7$ .............................. A61N 5/01; H01J 1/62
(52) U.S. Cl. ................ 313/489; 313/493; 607/94
(58) Field of Search .................. 607/88, 90–91; 250/504 R, 493, 494.1; 362/401; 313/489–493

(56) References Cited

U.S. PATENT DOCUMENTS

| | | | | |
|---|---|---|---|---|
| 4,600,009 | A | * | 7/1986 | Kramer et al. ............... 607/91 |
| 4,841,193 | A | * | 6/1989 | Nakamura et al. ...... 313/318.02 |
| 5,086,769 | A | * | 2/1992 | Vianello et al. ............. 607/94 |
| 5,585,688 | A | * | 12/1996 | DeKleine ............... 313/318.01 |
| 5,717,277 | A | * | 2/1998 | Siminovitch ........... 313/318.02 |
| 6,478,810 | B1 | * | 11/2002 | Purschel ...................... 607/91 |
| 6,494,901 | B1 | * | 12/2002 | Doty ........................... 607/91 |
| 6,828,720 | B2 | * | 12/2004 | Cavallaro et al. ........... 313/489 |
| 2002/0183810 | A1 | * | 12/2002 | Vlahos ........................ 607/94 |

OTHER PUBLICATIONS

*ETS, Inc. Your Partner In Tanning™ 2002 Professional Catalog*, ©2001 ETS Inc., Indianapolis, Indiana.

* cited by examiner

*Primary Examiner*—Roy D. Gibson
(74) *Attorney, Agent, or Firm*—Woodard, Emhardt, Moriarty, McNett & Henry LLP (57) ABSTRACT

In a preferred embodiment the present invention provides a tanning system with first and second units mounted to define a gap for a person to be tanned. The gap defines a head area to be adjacent the person's head and defines first and second shoulder areas oriented to be over the shoulders of a person. The first and second shoulder areas provide ultraviolet illumination, with a reduced amount of illumination provided in the head area. In one embodiment, the system includes a row of ultraviolet lamps mounted to the tanning device. Preferably the row includes two shoulder series, where the first shoulder series is over the first shoulder of the person to be tanned, and the second shoulder series is over the second shoulder of the person to be tanned. In preferred embodiments, the tanning system uses at least one quad lamp. In certain embodiments, the quad lamps are mounted vertically. In another preferred embodiment, the quad lamp includes four elongate portions. The elongate portions are connected in pairs. The quad lamp is oriented such that side portions of three of the elongate portions directly illuminate the location for the person to be tanned.

19 Claims, 9 Drawing Sheets

ULTRAVIOLET TANNING SYSTEMS

FIELD OF THE INVENTION

This invention relates to ultraviolet tanning. Examples of such devices include a tanning lamp, a tanning bed, tanning canopy, tanning booth, or face tanner. In particular, the invention relates to an improved lamp for tanning systems and an arrangement of lamps that is suitable for illuminating a person's shoulders.

BACKGROUND OF THE INVENTION

Arrangements of tubular ultraviolet fluorescent lamps have been used for, among other things, tanning beds, tanning booths, face tanners and tanning canopies. The present invention relates to an improved lamp for tanning systems and an arrangement of lamps for illuminating a user's shoulders. Typical tubular lamps, for example as used in tanning beds, require electrical connectors at opposing ends of the tubes. This requires electrical wiring and two sockets for each lamp, one at each end, adding to the cost and spacing requirements, limiting where such lamps can be mounted and requiring gaps between the bulbs.

Many types of tanning bed or booth systems have two or more portions which are movable between an open position and a closed position for the ease of access of the user. When the portions are in the operating position, a volume or gap is defined between them where the person to be tanned or treated is oriented. While the system's primary portions directly face the front and/or back of the person, typically there are no lamps directed towards the tops of the person's shoulders, leaving those areas with less coverage. One reason for this is due to the spacing and electrical difficulties in mounting tubular lamps spanning the gap between the system portions.

One approach to certain of these concerns has been to mount an additional portion off of the end of the system where the additional portion faces the gap area with an array of tubular bulbs. Typically these bulbs are oriented in the long direction of the gap area, i.e., in the plane of the user's shoulders, crossing over the person's head during use. While the lamps may be a preferred distance from the person's shoulders for optimum exposure, this can lead to excess heat and/or overexposure applied to the top of the person's head due to the comparative proximity of the top of the head to the lamps. This also leaves the central portion of the bulbs over the top portion of the person's head, whereas the preferred concentration points are over the user's shoulders.

A need exists for an improved lamp and a lamp arrangement. The present invention satisfies these needs and provides other important advantages.

SUMMARY OF THE INVENTION

An illustration of a preferred embodiment of the present invention is a tanning system. The tanning system includes a first unit and a second unit mounted to be positioned in an operating position with respect to the first unit such that the first and second units define a gap for a person to be tanned to be oriented. The gap defines a head area to be adjacent the person's head and defines separated first and second shoulder areas on opposing sides of said head area oriented to be over the shoulders of a person using the system. The first and second shoulder areas are operable to provide ultraviolet illumination towards a person, with a reduced amount of illumination provided in said head area.

In an alternate preferred embodiment, the present invention provides a system for tanning a person. The system includes a device defining a location for a person to be tanned; and a row of ultraviolet lamps mounted to the tanning device where the lamps are oriented to be over the tops of the two shoulders of the person to be tanned. Preferably the row includes two shoulder series, where the first shoulder series is oriented to be over the first shoulder of the person to be tanned, and the second shoulder series is oriented to be over the second shoulder of the person to be tanned. Preferably the first and second shoulder series are separated by an area oriented to be over or around the top of the person's head.

In a further preferred embodiment, the tanning system uses at least one quad lamp. In certain embodiments, the quad lamps are mounted vertically. In a still further embodiment, a tanning bed is provided using a vertical lamp.

In another preferred embodiment, a device for exposing a person to ultraviolet light, includes an ultraviolet quad lamp. The quad lamp includes four elongate portions, each elongate portion having a proximal portion, a side portion and a distal portion. The elongate portions are connected in pairs at their distal portions. The proximal portion of each elongate portion is connected to a base. The device includes a location for a person to be tanned adjacent to the quad lamp. The quad lamp is oriented such that the side portions of three of the elongate portions directly illuminate the location for the person to be tanned.

It is an object of certain embodiment of the present invention to provide an improved lamp for use in ultraviolet illumination systems.

It is an object of certain other embodiments of the present invention to provide tanning systems and devices providing ultraviolet illumination to the shoulders of a user.

Further objects, features and advantages of the present invention shall become apparent from the detailed drawings and descriptions provided herein.

DESCRIPTION OF THE ILLUSTRATIVE EMBODIMENTS

For the purposes of promoting an understanding of the principles of the invention, reference will now be made to the embodiment illustrated in the drawings and specific language will be used to describe the same. It will nevertheless be understood that no limitation of the scope of the invention is thereby intended. Any alterations and further modifications in the described device, and any further applications of the principles of the invention as described herein are contemplated as would normally occur to one skilled in the art to which the invention relates.

Traditionally, ultraviolet illumination/radiation systems come in variety of configurations, including beds, booths, canopies and facial systems. These are often used by people to achieve the cosmetic affect of suntanned looking skin, or are often used for the medical benefits such as absorbing vitamin D. The present invention provides an improved lamp for use in such systems and provides an improved method of mounting lamps for more effective coverage of the person using the system. For explaining the present invention, a tanning bed and tanning booth are described in detail with references to a "person to be tanned;" however, it will be understood that this is not by way of limitation and various types of cosmetic and therapy systems and their users are being described. References herein to "ultraviolet illumination" are intended to mean the emission of radiation in the ultraviolet spectrum desired for tanning, and are not references to visible illumination, although visible illumination may be a by-product.

Figure 1:
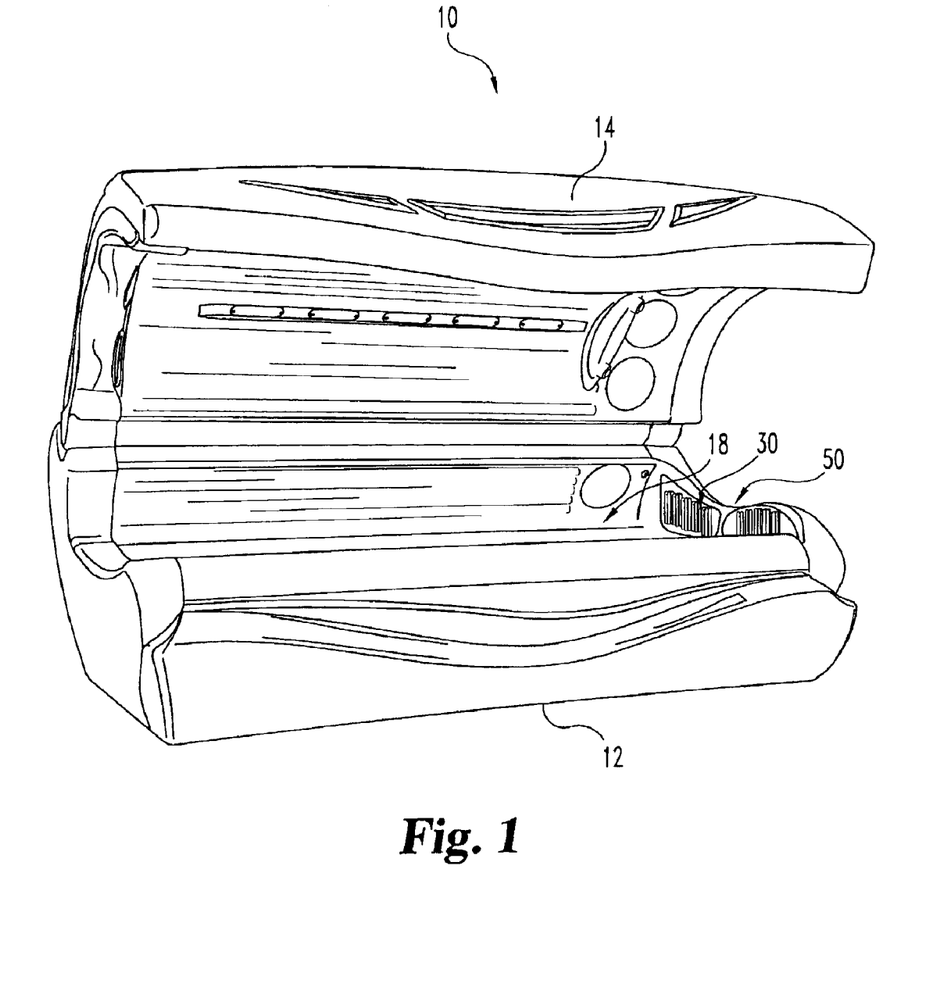
FIG. 1 is a perspective view of a tanning bed according to one preferred embodiment of the present invention.
Figure 2:
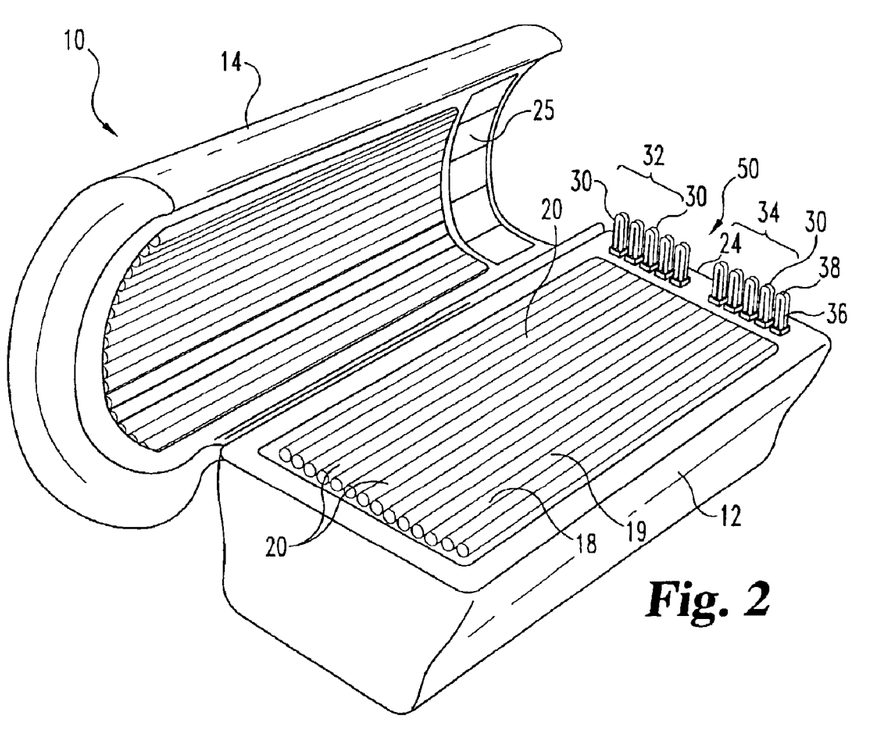
FIG. 2 is an alternate perspective view of the embodiment of FIG. 1.
Figure 3:
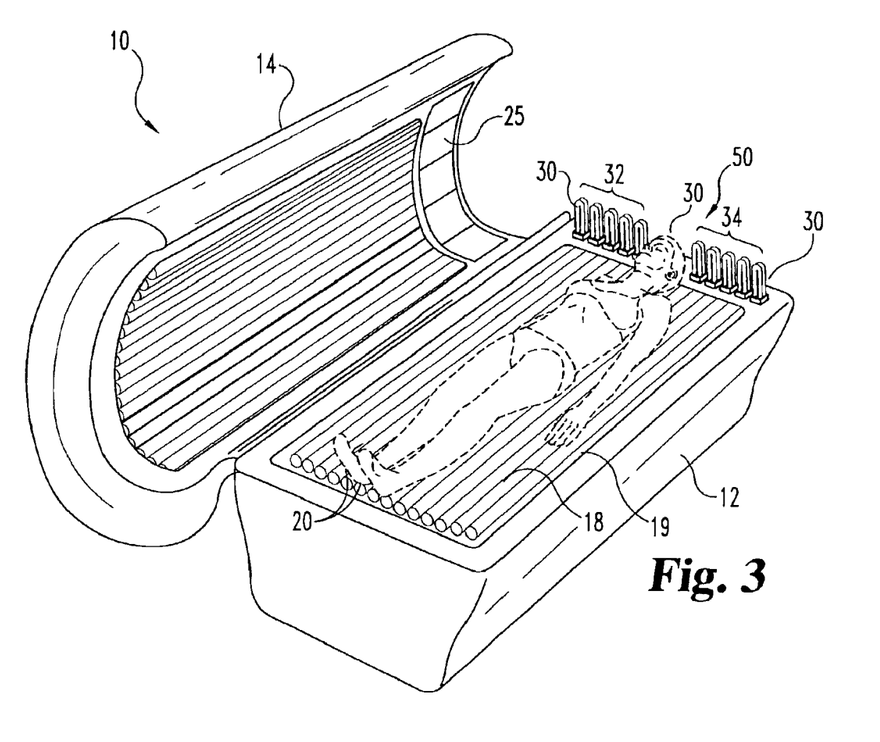
FIG. 3 is the view of FIG. 2, illustrating a user in position in the tanning system.

Referring to FIGS. 1–3, a tanning system, such as bed 10, is illustrated. Bed 10 incorporates one standard style of a tanning bed plus illustrates the present invention. A standard bed often includes a lower or base unit 12 and an upper unit or canopy 14. Within each of the base unit 12 and canopy 14 are typically a plurality of parallel, elongate, tubular bulbs or lamps 20. Bulbs 20 are typically fluorescent ultraviolet producing bulbs. Base unit 12 defines a support or bed surface 18 for a person to lie during the application process. The person to be tanned typically lies with the person's back to the support surface and facing the canopy. In many instances, support surface 18 includes an acrylic shield 19 which is transparent to UV radiation, and which separates the user from bulbs 20.

Often the upper unit or canopy 14 is pivotally mounted to base unit 12 to allow the user ease of access to enter and lie upon support surface 18. To place the system in an operating position, the canopy is closed to a selected distance defining a gap or volume between the base unit 12 and canopy 14. The person to be tanned is oriented in this gap. As an optional feature, specialized facial tanning units 25 are placed in the canopy 14 in an area adjacent the person's face.

FIGS. 1–3 further show a plurality of lamps 30 illustrating one embodiment of the present invention. Shown in detail is a row of lamps 30 generally across the top edge 24 of bed 10. Preferably in one embodiment lamps 30 are quad lamps. Lamps 30 are arranged to span a substantial portion of the gap between base unit 12 and upper unit 14 when bed 10 is in its closed or operating position.

Shoulder zones are preferably defined within the gap between base unit 12 and canopy 14. The illumination from the shoulder zones with a person is illustrated in a preferred arrangement shown FIG. 3. For ease of reference, the shoulder zones are referred to as oriented "over" or facing "the tops" of the person's shoulder which is defined with respect to the person and not an absolute direction. The area of the shoulder referred to is generally the portion extending between the person's neck and arm and extending between the person's torso and back. For ease of reference, the person's head generally defines an "up" direction with the person's feet defining an opposing "down" direction."

In this embodiment, ultraviolet lamps 30 are arranged along the upper edge 24 of base unit 12 such that the sides of the lamps 30 face the tops of the two shoulders of the person to be tanned. Preferably, lamps 30 include a first series 32 and a second series 34 mounted in shoulder areas oriented to be over the shoulders of the person to be tanned. Preferably, head space 50 is defined between first series 32 and second series 34. Head space 50 preferably has a width equal to or greater than the top of the user's head. "Series" refers to one or more bulbs. In a preferred range, each series includes one to seven bulbs, and in a more preferred range, each series includes four or five bulbs.

Figure 6:
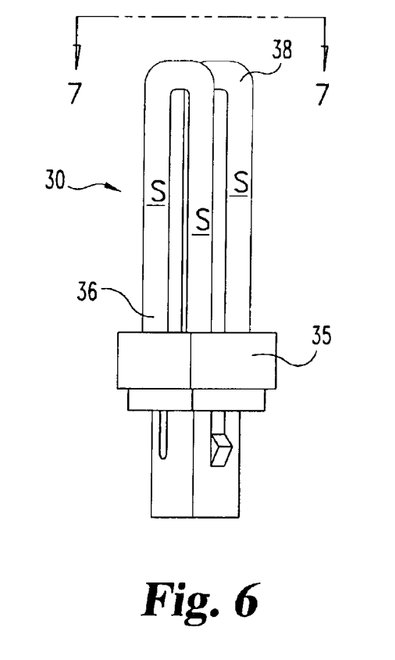
FIG. 6 is a side view of a preferred embodiment of a quad lamp.

In a preferred embodiment, lamps 30 are mounted with a proximal end 36 in a base 35 adapted to fit into a socket and extend vertically from base unit 12 to a distal lamp portion 38 (FIG. 6). In a less preferred alternative, lamps 30 extend downward from canopy 14. In a further alternate embodiment, lamps 30 can be mounted horizontally or at angles across the gap.

Figure 4:
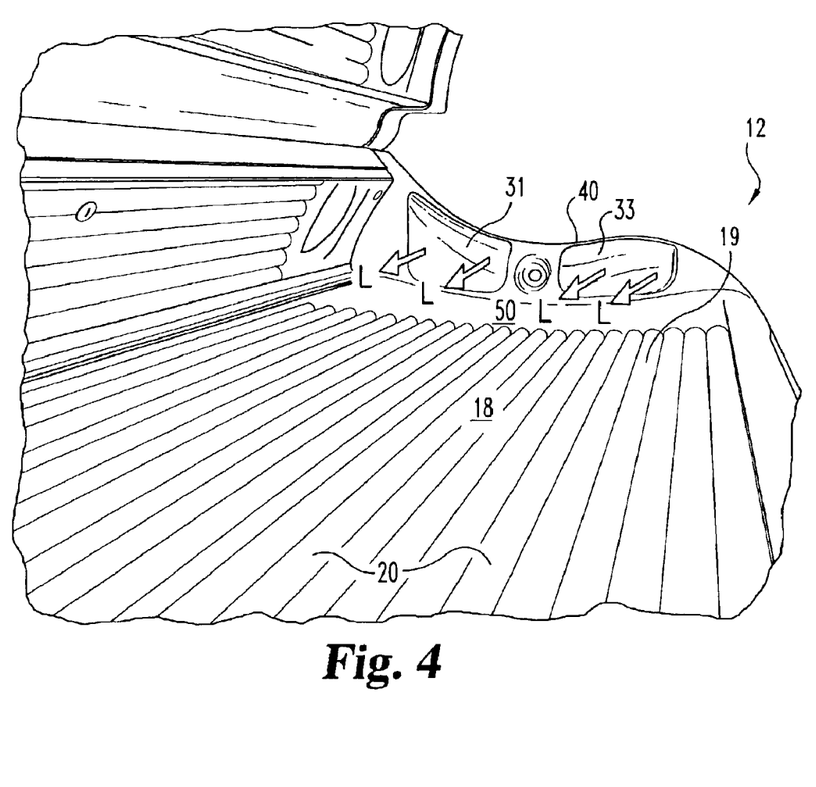
FIG. 4 is a partial view of one end of a tanning system according to an one preferred embodiment of the present invention.

One view of the head end of a bed 10 with shoulder zones 31 and 33 is illustrated in FIG. 4. The head end of base 12 includes a head area 50 for the user's head to be oriented. The head end further includes a first shoulder zone 31 and a second shoulder zone 33. Preferably ultraviolet light is emitted from shoulder zones 31 and 33 in direction L towards the user's shoulders. In certain preferred embodiments, shoulder zones include ultraviolet fluorescent lamps, however other ultraviolet sources, such as mercury lamps could alternately be used. According to certain preferred embodiments of the present invention, the ultraviolet light emitted in direction L in a defined head area 50 is reduced or blocked. In one embodiment, head area 50 is formed by a distance separating the illumination sources in the shoulder zones. Head area 50 can alternately be defined by a blocking member, such as a solid or semi-transparent panel, covering or blocking the illumination sources.

Figure 5A:
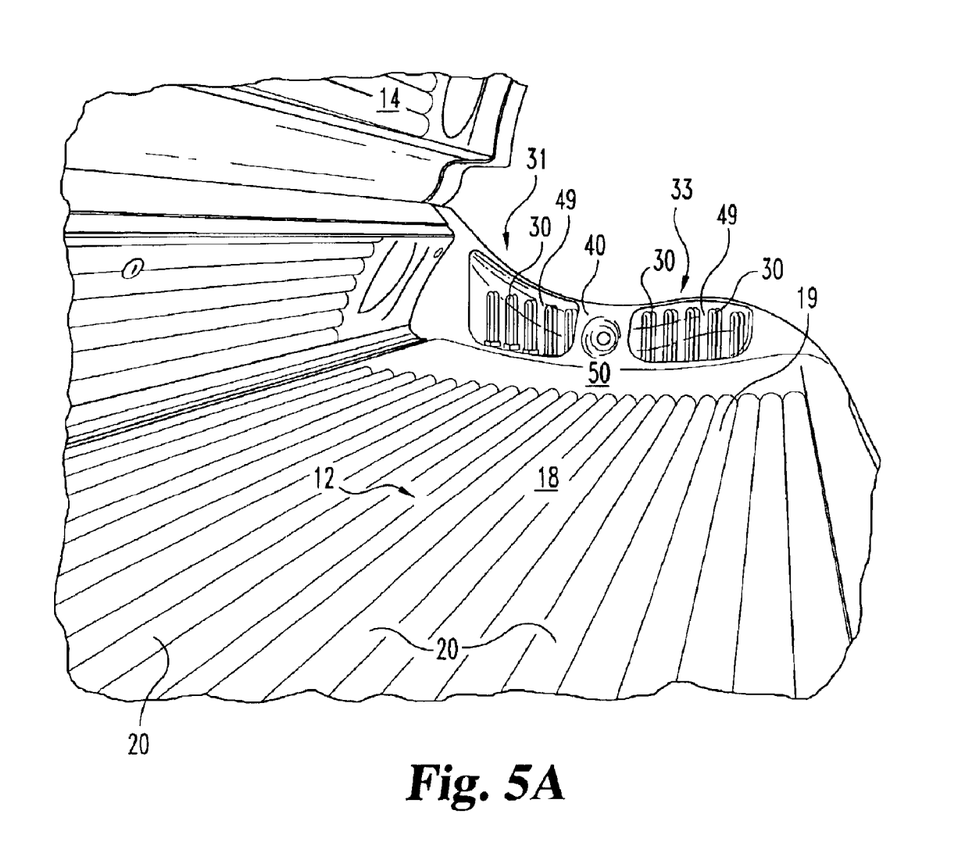
FIG. 5A is a partial view of one end of a tanning system according to one preferred embodiment of the present invention.
Figure 5B:
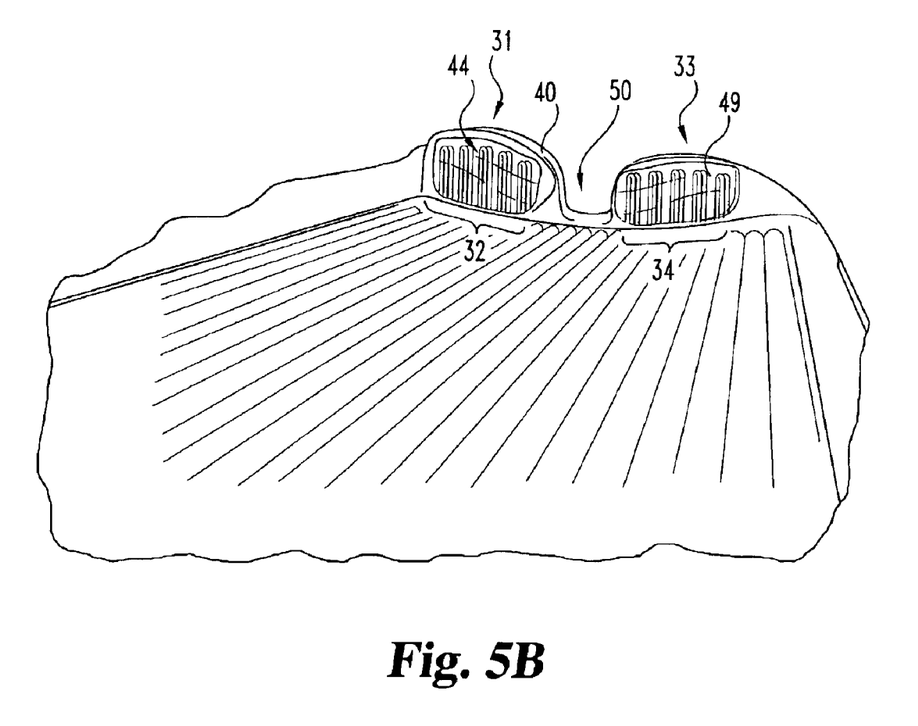
FIG. 5B is a partial view of one end of a tanning system according to an alternate preferred embodiment of the present invention.

As illustrated in specific embodiments in FIGS. 5A and 5B preferably, lamps 30 in shoulder zones 31 and 33 are protected by a cover 40 or 40', including a sheet of transparent acrylic 49 mounted between the lamps 30 and support surface 18. This protects the lamps from breakage as well as preventing burns to the user. As an optional feature, cover 40 or 40' can incorporate one or more internal reflectors 44 to reflect ultraviolet light emitted from the rear of lamps 30 back towards the person to be tanned. Cover 40 or 40' can preferably be made with a thin upper cross-section over the lamps, since wiring and sockets do not need to be mounted at the distal ends 38 of the lamps. Cover 40 assists to define a head area 50, or in an alternate embodiment of cover 40', the cover includes a contoured area 50' upon which the user's head can be laid.

Figure 7:
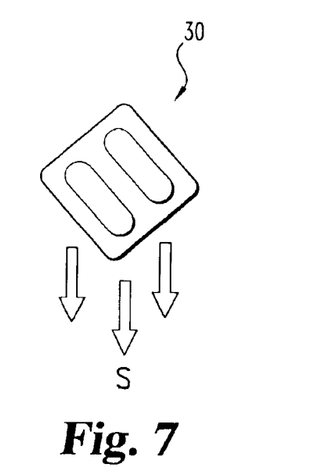
FIG. 7 is a top down view of the quad lamp of FIG. 6 taken along line 7—7.
Figure 8:
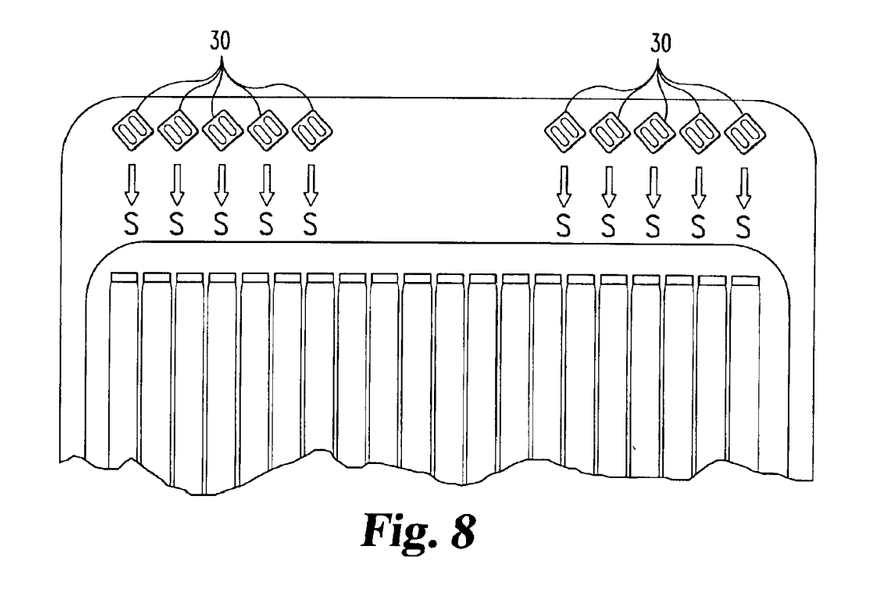
FIG. 8 is a partial top-down view of one end of a tanning system illustrating the orientation of the quad lamp of FIG. 6 in a bed according to one preferred embodiment of the present invention.

Preferably, lamps 30 are quad lamps treated to provide ultraviolet radiation in the desired spectral range. A specific preferred embodiment of a quad lamp is illustrated in FIGS. 6–8. The quad lamp in FIG. 6 includes a base 35 attachable to an electric socket. Extending from and returning to the base are one or more tubes with a proximal portion 36 and a distal portion 38 containing a gas and treated to fluoresce.

In one preferred embodiment, each lamp includes two "U" shaped tubes arranged in a parallel pattern. In an alternate embodiment, the "U" tubes are in a cross or "X" pattern. Further shapes for the tubes, such as spirals, twists and curves, are also possible as desired. One example of a suitable UV quad lamp is a Wolff System® MARQUIS model 2-pin compact fluorescent lamp, Model CF26W, No. 20699.

In one preferred orientation shown in FIGS. 6–8, the quad lamps 30 are mounted with a side towards the person such that the sides of three tube portions are directed to fluoresce towards the person to be tanned's shoulders (direction "S"). The side of the lamp is intended to mean a direction perpendicular to the length of the longer "U" legs. It has been found that in this orientation, the Te for a 26 watt quad lamp is approximately 10.5 minutes. In a less preferred orientation, only two tube portions directly face the person's shoulders, which for a 26 watt bulb creates a Te of approximately 12.7 minutes. In alternate embodiments, a 13 watt bulb had a Te of approximately 24.6 minutes and a 36 watt bulb had a Te of 63.2 minutes.

In an alternate arrangement (FIG. 5) first series 32 and second series 34 of lamps 30 are inset from upper edge 24 of the base 12. In this arrangement, a gap separates the series to allow for the person's head, and each shoulder series of lamps is located in closer proximity to the person's shoulders. In this arrangement, the shoulder lamps series may be uncovered, or a contoured cover 40' with acrylic shields may be placed to cover all of the lamps. Preferably cover 40' includes a contoured "dip" or head area 50' for the person's head, minimizing direct UV exposure to the sides of the person's head and neck.

Figure 9:
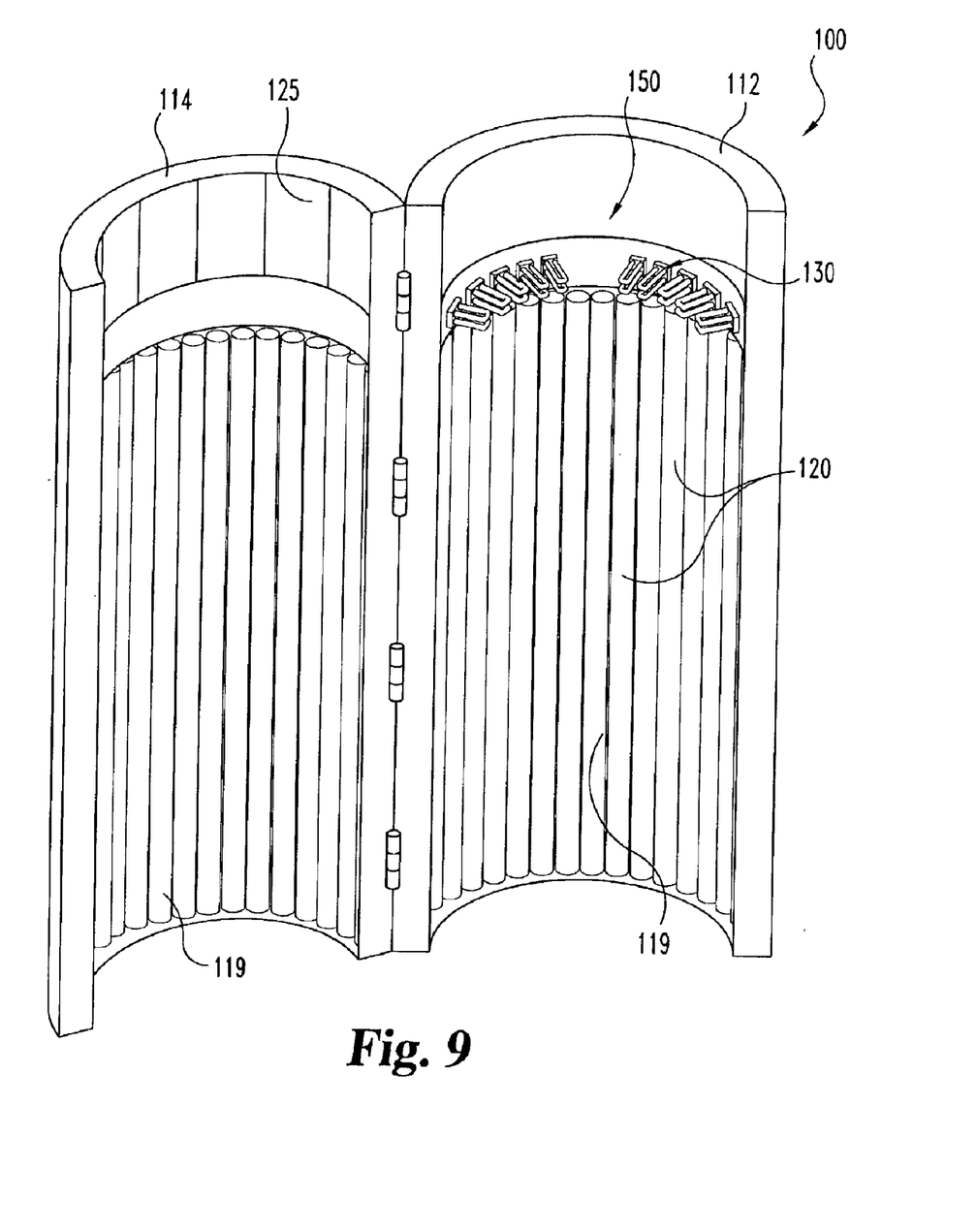
FIG. 9 is a perspective view of an alternate preferred embodiment of a tanning system.

In a still further embodiment, illustrated in FIG. 9 is a tanning system booth 100 incorporating a preferred embodiment of the present invention. Booth 100 includes a first or "back" portion 112 and a second or "front" portion 114 hingedly mounted to back portion 112. In an alternate option (not shown) front portion 114 may be divided into two portions hinged to opposing sides of back portion 112. Booth 100 is movable from an open position for ease of access to a closed or "operating" position. When booth 100 is in the operating position, a gap or volume is defined between back portion 112 and front portion 114. A person to be tanned preferably stands within this volume during a tanning session and preferably is substantially encircled by the booth 100. Mounted within back portion 112 and front portion 114 are a plurality of elongate, tubular tanning bulbs 120. Bulbs 120 are separated from the user by UV transparent acrylic shields 119, or alternately wire mesh grids. Front portion 114 optionally includes a specialized facial tanner 125.

Illustrated with an end-on view within booth 100 of FIG. 9, are shoulder portions to illuminate a person's shoulders. In one embodiment, the shoulder portions include one or more shoulder lamps 130, and in one preferred embodiment, shoulder lamps 130 are quad lamps. Shoulder lamps 130 are preferably oriented to provide direct exposure to the user's shoulders during use. Shoulder lamps 130 preferably extend outwardly from back portion 112, substantially perpendicular to elongate bulbs 120. When booth 100 is in its operating position, lamps 130 preferably substantially span the gap between back portion 112 and front portion 114. For the user's comfort, a head gap 150 is arranged between the shoulder portion, separating lamps 130 into a first and second series of lamps. Lamps 130 may be mounted adjacent the upper edge of booth 100, or inset along the height of booth 100 (as shown) to be closer to the user's shoulders. In an optional arrangement lamps 130 are mounted on adjustable tracks (not shown) and the height and/or width of head gap 150 of lamps 130 is adjustable to an optimized position for a particular user's size. Preferably, lamps 130 are separated from the user with a minimum distance plus an acrylic cover or mesh grid (not shown).

Figure 10:
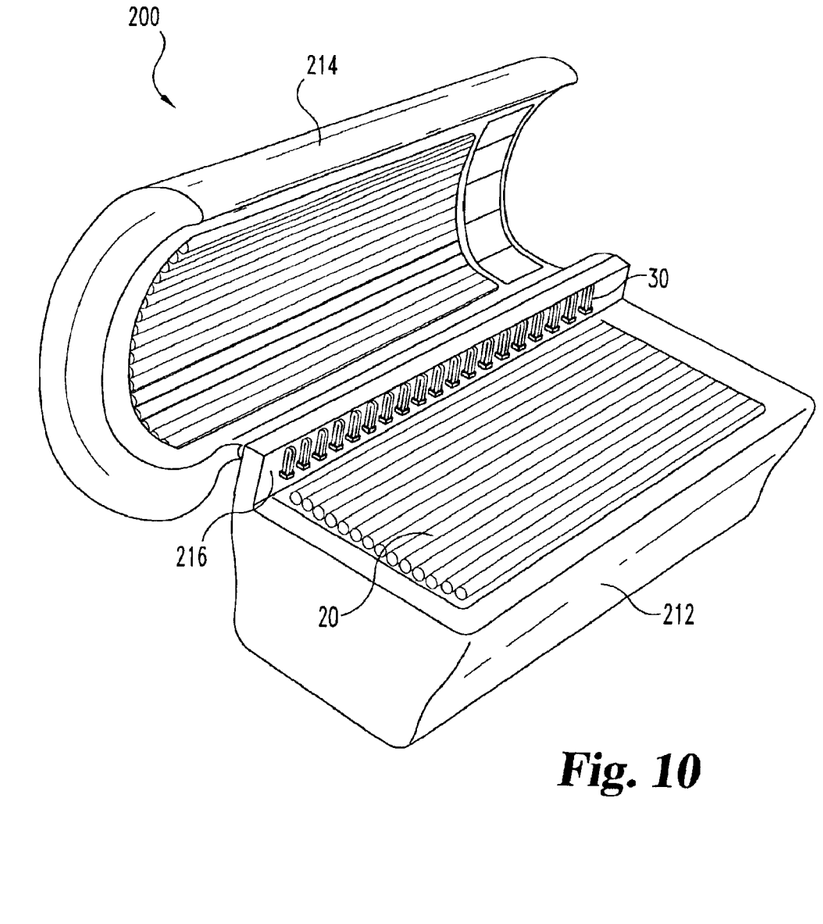
FIG. 10 is a perspective view of a still further preferred embodiment of a tanning system.

In addition to use as shoulder lamps, quad lamps according to the present invention can be used in alternate locations in tanning systems. For example, as shown in FIG. 10, some bed models 200 incorporate a side panel 216 extending between the base 212 and canopy 214 alongside the user. Quad lamps 30 can be mounted vertically or horizontally within such side panels 216. Use of such lamps allows electrical sockets and wiring to be eliminated from the panel area opposite the quad lamp base, or alternately allows the lamp base locations to be alternated, allowing for a greater density of lamps with minimum spacing separation. In a still further embodiment, quad lamps may be mounted in arrays as a substitute for elongate tubular lamps. Such an array of lamps allows ease of access to the lamp for installation and replacement, and lamps can be replaced individually as needed.

As a further advantage, quad lamps can be packaged, shipped and stored in compact cartons, saving in shipping and storage costs over elongate bulbs which frequently have awkward lengths and require special handling.

While the invention is shown in the preferred context of a tanning bed, the concepts of many of the patent claims also encompass tanning booths, tanning canopies, facial tanners and other devices which emit tanning light, as well as therapy light emitting devices without significant ultraviolet light such as may be used to lower bilirubin levels in infants, or to treat seasonal affective disorder in adults.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A tanning bed defining a generally horizontal location for a person to lie, comprising at least one vertically oriented tanning lamp wherein said lamp is arranged to emit ultraviolet radiation substantially horizontally towards a person in the horizontal location.

2. A tanning bed, comprising:
   a) a base unit defining a bed area for a person to lie;
   b) wherein said base unit defines a head area to be adjacent the person's head and defines first and second shoulder areas on opposing sides of said head area oriented to be over the shoulders of a person lying upon said base unit;
   c) wherein said first and second shoulder areas are operable to provide ultraviolet illumination towards a person; and,
   d) wherein a reduced amount of illumination is provided in said head area.

3. The tanning bed of claim 2, wherein said illumination is provided by at least one lamp mounted within said first shoulder area, and at least a second lamp mounted within said second shoulder area.

4. The tanning bed of claim 3, wherein said first and second lamps are vertically mounted.

5. The tanning system of claim 4, said first and second lamps are quad lamps.

6. The system of claim 2, wherein said head area is defined by a distance separating said first and second shoulder areas.

7. The system of claim 2, wherein said head area is defined by a panel separating said first and second shoulder areas.

8. A tanning system, comprising:
 a) a first unit;
 b) a second unit mounted to be positioned in an operating position with respect to said first unit such that said first and second units define a gap for a person to be tanned to be oriented;
 c) wherein said gap defines a head area to be adjacent the person's head and defines separated first and second shoulder areas on opposing sides of said head area oriented to be over the shoulders of a person using the system;
 d) wherein said first and second shoulder areas are operable to provide ultraviolet illumination towards a person; and,
 e) wherein a reduced amount of ultraviolet illumination is provided in said head area.

9. The tanning system of claim 8, wherein said illumination is provided by at least one lamp mounted within said first shoulder area, and at least a second lamp mounted within said second shoulder area.

10. The tanning system of claim 9, wherein said first and second lamps are vertically mounted.

11. The tanning system of claim 9, wherein said first and second lamps are quad lamps.

12. The tanning system of claim 9, wherein said illumination is provided by a first series of lamps mounted within said first shoulder area, and a second series of lamps mounted within said second shoulder area.

13. The tanning system of claim 12, wherein said first and second series of lamps include quad lamps.

14. The system of claim 8, wherein said head area is defined by a distance separating said first and second shoulder areas.

15. The system of claim 8, wherein said head area is defined by a panel separating said first and second shoulder areas.

16. A system for tanning a person, comprising,
 a) a device defining a location for a person to be tanned;
 b) a row of ultraviolet lamps mounted to said tanning device and oriented to be over the top of the two shoulders of the person to be tanned;
 c) wherein said row includes two shoulder series, wherein said first shoulder series is oriented to be over the first shoulder of the person to be tanned, said second shoulder series is oriented to be over the second shoulder of the person to be tanned; and,
 d) wherein said first and second shoulder series are separated by a distance oriented to be over the person's head.

17. The tanning system of claim 16, wherein said first shoulder series and said second shoulder series each include one to seven lamps.

18. The tanning system of claim 17, wherein said first shoulder series and said second shoulder series each include five lamps.

19. A device for exposing a person to ultraviolet light, comprising:
 a) an ultraviolet quad lamp;
 b) wherein said quad lamp includes four elongate portions, each elongate portion having a proximal portion, a side portion and a distal portion and wherein said elongate portions are connected in pairs at said distal portions;
 c) a base, wherein said proximal portion of each elongate portion is connected to said base;
 d) a location for a person to be tanned adjacent said quad lamp; and,
 e) wherein said quad lamp is oriented such that the side portions of three of said elongate portions directly illuminate the location for the person to be tanned.

* * * * *